United States Patent
Li et al.

(10) Patent No.: US 8,442,619 B2
(45) Date of Patent: May 14, 2013

(54) SYSTEM AND METHOD FOR DETECTING ERRORS IN POSITION TRACKING SYSTEMS USED FOR MEDICAL APPLICATIONS

(75) Inventors: Dun Alex Li, Salem, NH (US); Joseph Casey Crager, Newton, MA (US); Douglas Karl Johnson, Hampton, NH (US)

(73) Assignee: General Electric Company, Schenectady, NY (US)

( * ) Notice: Subject to any disclaimer, the term of this patent is extended or adjusted under 35 U.S.C. 154(b) by 1889 days.

(21) Appl. No.: 11/468,481

(22) Filed: Aug. 30, 2006

(65) Prior Publication Data

US 2008/0121703 A1 May 29, 2008

(51) Int. Cl.
*A61B 5/00* (2006.01)
(52) U.S. Cl.
USPC ........... 600/424; 600/407; 600/410; 600/417; 600/425; 600/429; 606/130
(58) Field of Classification Search .................. 600/424, 600/425; 606/130
See application file for complete search history.

(56) References Cited

U.S. PATENT DOCUMENTS

| 5,676,673 A | 10/1997 | Ferre et al. |
| 2004/0220471 A1* | 11/2004 | Schwartz ...................... 600/424 |
| 2007/0167741 A1* | 7/2007 | Sherman et al. .............. 600/424 |
| 2008/0125646 A1* | 5/2008 | Govari et al. ................. 600/424 |

* cited by examiner

*Primary Examiner* — Unsu Jung
*Assistant Examiner* — Amanda Lauritzen
(74) *Attorney, Agent, or Firm* — McAndrews, Held & Malloy, Ltd.; William Baxter

(57) ABSTRACT

A system and method for identifying errors while tracking instrument navigations is enclosed. The method may include assigning a plurality of virtual points to a plurality of sensors. At least one of the virtual points may be a non-fixed virtual point. The assignment of virtual points to sensors may be determined based on the medical instrument, or the medical instrument attachment, being used. Virtual point locations may be determined for the non-fixed virtual point. The locations of the non-fixed virtual point may be determined based on the medical instrument, or the medical instrument attachment, being used. The vector values for vectors terminating at the non-fixed virtual point may be adjusted. The field integrity values for the virtual points may be computed. If a field integrity value is greater than a threshold value, an error signal may be communicated.

18 Claims, 6 Drawing Sheets

SYSTEM AND METHOD FOR DETECTING ERRORS IN POSITION TRACKING SYSTEMS USED FOR MEDICAL APPLICATIONS

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

INCORPORATION BY REFERENCE

Applicant hereby incorporates by reference in its entirety U.S. Pat. No. 5,676,673 which is assigned to the assignee of the present application.

BACKGROUND OF THE INVENTION

The present invention generally relates to an electromagnetic tracking system. In particular, the present invention relates to an improved system and method for detecting errors in the electromagnetic tracking system.

Many medical procedures involve a medical instrument, such as a drill, a catheter, scalpel, scope, shunt or other tool. In some cases, a medical imaging or video system may be used to provide positioning information for the instrument. However, medical practitioners often do not have the use of medical imaging systems when performing medical procedures. The use of medical imaging systems for instrument tracking may be limited for health and safety reasons (e.g., radiation dosage concerns), financial limitations, physical space restrictions, and other concerns, for example.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

While various tracking systems and methods have been developed for monitoring the position of medical instruments with respect to a patent's anatomy, current systems and methods are not perfectly accurate for all clinical applications. For example, optical tracking systems are sensitive to objects, e.g. draping, blood, contamination, obstructing the view of the optical reflectors. Electromagnetic (EM) tracking systems generally do not have line of sight problems. The presence of metallic or ferromagnetic objects nearby the EM transmitters (Tx) or receivers (Rx), however, may distort the transmitting EM fields. Such a distortion may result in inaccurate tracker position and orientation (P&O) measurements. To mitigate the risk, such navigation systems usually have an error detection mechanism to monitor the quality of the tracker P&O updates and report warning messages to the system and/or user to disable the navigation assistance if a malfunction is detected.

Current error detection mechanisms for detecting EM distortion, however, may have high rates of false occurrences. For example, current error detection systems and methods may indicate the presence of an error in the EM tracking system when, in actuality, no error is present. A high rate of false occurrences may be disruptive to the user. For instance, a high rate of false occurrences may be disruptive during surgery or other medical procedure. Also, a high rate of false occurrences may undermine the accurateness of the tracking system in the mind of the user in such a way that the user may not trust the tracking system. Accordingly, a surgical procedure may be more invasive than necessary.

Thus, a need exists for a surgical navigation system and method that allows for surgical or other medical procedures to be performed in a more reliable and less invasive manner. A tracking system and method that operates with a more accurate error detection system and method would be highly desirable. Such a system and method may be easily adjustable and configurable. Such a system and method may provide a more accurate detection of EM distortion, and thus a more accurate detection of system errors.

BRIEF SUMMARY OF THE INVENTION

Certain embodiments of the present invention may include a tracking system for instrument navigation. The system may include a transmitter for transmitting a signal. The signal may identify transmitter coordinates. The system may also include a field sensing unit for determining the location of the field sensing unit within the transmitter coordinates. The field sensing unit may have a plurality of sensors. The plurality of sensors may create a plurality of virtual points. At least one of the virtual points may be a non-fixed virtual point. The system may also include a processor for processing field integrity detection values for the virtual points.

In an embodiment, the instrument may be a medical instrument, the transmitter may be attached to patient anatomy and the field sensing unit may be attached to the medical instrument. The location of the non-fixed virtual point may be determined based on the medical instrument in use. The location of a non-fixed virtual point may also be based on the attachment in use for the medical instrument in use. In an embodiment, the location of a non-fixed virtual point is at the tip of the medical instrument. The tip of the medical instrument may be used for insertion into a patient anatomy.

Certain embodiments of the present invention may include a tracking system for medical instrument navigation. The system may include a transmitter for transmitting a signal. The signal may identify transmitter coordinates. The system may also include a field sensing unit for determining the location of the field sensing unit within the transmitter coordinates. The field sensing unit may have a more than two sensors. The system may also include a processor for processing field integrity detection values for the virtual points.

In an embodiment, the sensors may create a plurality of virtual points. At least one of the virtual points may be a non-fixed virtual point. The location of the non-fixed virtual point may be determined based on the medical instrument in use. The location of a non-fixed virtual point may also be based on the attachment in use for the medical instrument in use. In an embodiment, the location of a non-fixed virtual point is at the tip of the medical instrument. The tip of the medical instrument may be used for insertion into a patient anatomy.

Certain embodiments of the present invention may include a method for instrument navigation. The method may include assigning a plurality of virtual points to a plurality of sensors. At least one of the virtual points may be a non-fixed virtual point. The method may also include determining virtual point locations for the non-fixed virtual point. The method may also include adjusting vector values for vectors terminating at the non-fixed virtual point. The method may also include computing field integrity values for the plurality of virtual points. The method may also include communicating an error signal if a field integrity value is greater than a threshold value.

In an embodiment, the instrument may be a medical instrument. The step of assigning may include indicating the medical instrument being used to computer software. The step of assigning may also include indicating the attachment being used for the medical instrument to computer software. The step of determining virtual point locations may include determining virtual point locations based on the medical instrument being used. The step of determining virtual point locations may include determining virtual point locations based on the medical instrument attachment being used. In an embodiment, the instrument may be a field sensing unit for use with virtual reality computer software.

BRIEF DESCRIPTION OF SEVERAL, VIEWS OF THE DRAWINGS

Figure 1:
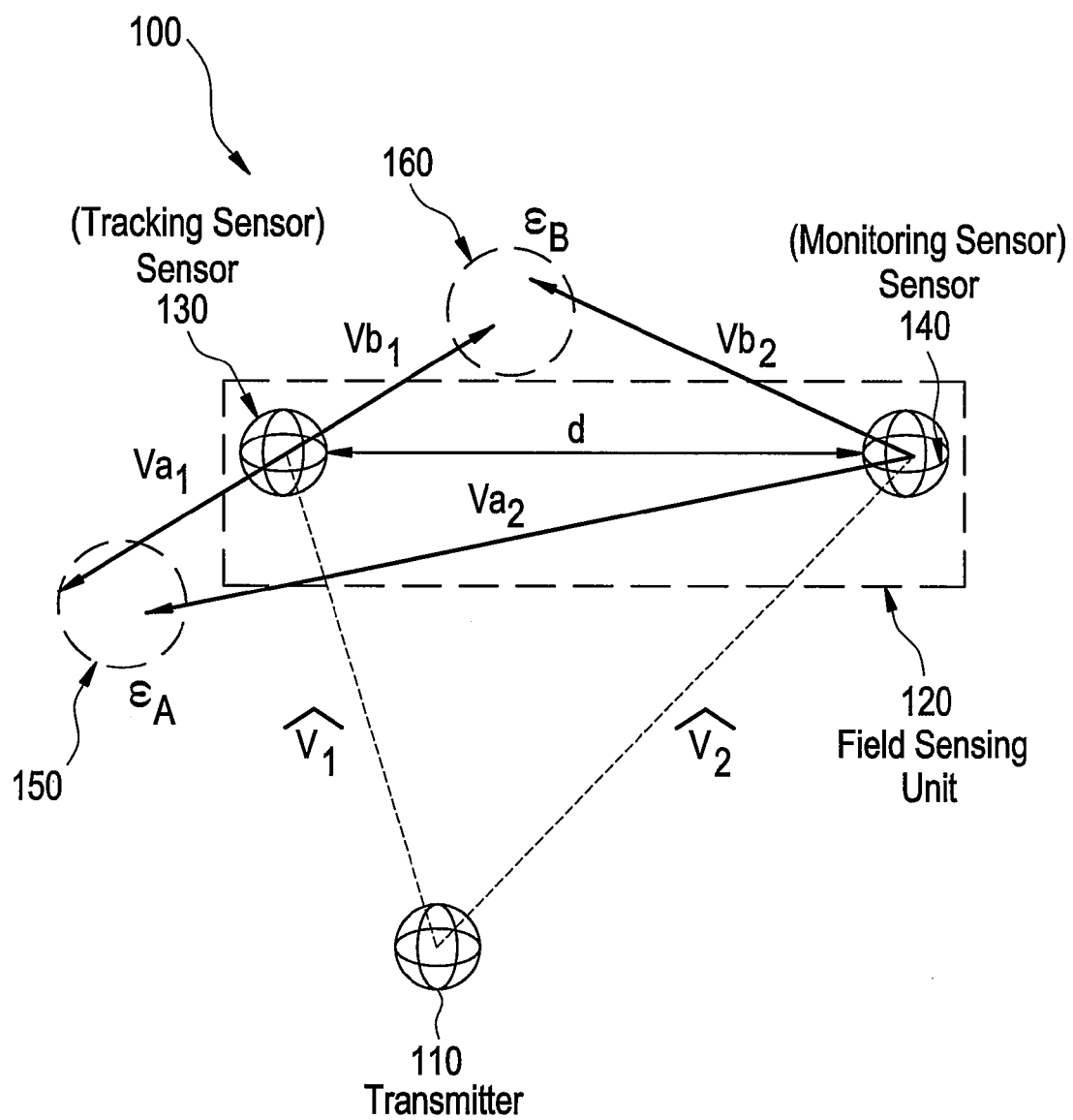
FIG. 1 illustrates a vector model of an electromagnetic tracking system

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references embodiments of an electromagnetic tracking system used with an image-guided surgery system. It is understood that the present invention may be used with other embodiments, including various combinations of sensors and virtual points, with other imaging systems, with other tracking systems, and with other applications.

An electromagnetic (EM) tracking system may be utilized as part of an image-guided surgery system. For example, an EM tracking system may be utilized as described in U.S. Pat. No. 5,676,673 which is hereby incorporated by reference in its entirety.

FIG. 1 illustrates a vector model of an electromagnetic tracking system 100 having architecture of two sensors 130 and 140 and two virtual points 150 and 160. The tracking system 100 includes a transmitter 110 and a field-sensing unit 120. In an embodiment, the transmitter 110 may be attached to patient anatomy. Additionally, in an embodiment, the field-sensing unit 120 may be attached to a medical instrument. As illustrated in FIG. 1, the field-sensing unit 120 may include two sensors, a tracking sensor 130 and a monitoring sensor 140. The sensors 130 and 140 may be separated by a fixed distance d.

As illustrated by the vector model in FIG. 1, the tracking sensor 130 and the monitoring sensor 140 may each project virtual vectors. The virtual vectors generally begin at a sensor and terminate at a virtual point. The termination point of a virtual vector may be a virtual tip ($V_{tip}$). A virtual tip may have a range of values and still be within a virtual point.

For example, the tracking sensor 130 may project vectors $V_{a1}$ and $V_{b1}$. The monitoring sensor 140 may project vectors $V_{a2}$ and $V_{b2}$. Two virtual points are illustrated in FIGS. 1, 150 and 160. The scope of each of the virtual points is represented by circles 150 and 160, respectively. As shown in FIG. 1, the $V_b$ vectors project to virtual point 150. The $V_a$ vectors project to virtual point 160. The distance between the tips of the $V_a$ vectors is distance $\epsilon_A$. The distance between the tips of the $V_b$ vectors is distance $\epsilon_B$. As sensors 130 and 140 are separated by a fixed distance d, the value of vectors $V_{a1}$, $V_{b1}$, $V_{a2}$, and $V_{b2}$ to remain at virtual points 150 and 160 may be determined as part of a factory calibration in a distortion free environment. The value of vectors $V_{a1}$, $V_{b1}$, $V_{a2}$, and $V_{b2}$ may be monitored as a medical instrument navigates through the transmitter coordinate system. In an embodiment, the vectors $V_{a1}$, $V_{b1}$, $V_{a2}$, and $V_{b2}$ may be monitored according to the following equations:

$$\hat{V}a_{(1)} = \hat{V}_1 + \hat{q}_1 \cdot V\text{tip}_{a1} \cdot \hat{q}_1^*$$

$$\hat{V}b_{(1)} = \hat{V}_1 + \hat{q}_1 \cdot V\text{tip}_{b1} \cdot \hat{q}_1^* \quad \text{Equation (1)}$$

$$\hat{V}a_{(2)} = \hat{V}_2 + \hat{q}_2 \cdot V\text{tip}_{a2} \cdot \hat{q}_2^*$$

$$\hat{V}b_{(2)} = \hat{V}_2 + \hat{q}_2 \cdot V\text{tip}_{b2} \cdot \hat{q}_2^* \quad \text{Equation (2)}$$

where $V_1$, $V_2$ and $q_1$, $q_2$ are Position and Orientation readings from sensor 130 and sensor 140, respectively. The $V_{tip}$ values represent the location of the tip of each of the respective vectors.

As shown in FIG. 1, the difference between the vectors at each virtual point may be monitored. If the difference between the measured locations for either virtual point is greater than a predetermined value ($\epsilon$), then a field integrity violation message may be displayed and normal operation of the system may be suspended. For example, a test on the integrity of the transmitter field may be determined by the following equation:

Test on Field Integrity Detection (FID):

$$\text{Test} = \begin{cases} FID\ 1 = |\hat{V}a_{(tip\,2)} - \hat{V}a_{(tip\,1)}| > \varepsilon A \\ \text{or} \\ FID\ 2 = |\hat{V}b_{(tip\,2)} - \hat{V}b_{(tip\,1)}| > \varepsilon B \end{cases} \quad \text{Equation (3)}$$

A quantifiable level of FID may be used to determine the presence of potential error sources, such as metal distortion caused by the presence of a medical instrument. In an embodiment, a processor may perform the FID calculations. For example, if the FID is greater than a predetermined value ($\epsilon$), the presence of an error condition may be indicated to a user. For example, if FID 1 is greater than a distance $\epsilon_A$ the system 100 may alert the user that an error condition is present and the navigation system is not currently accurate. In addition, for example, if FID 2 is greater than a distance $\epsilon_B$ the system 100 may alert the user that an error condition is present and the navigation system is not currently accurate.

Figure 2:
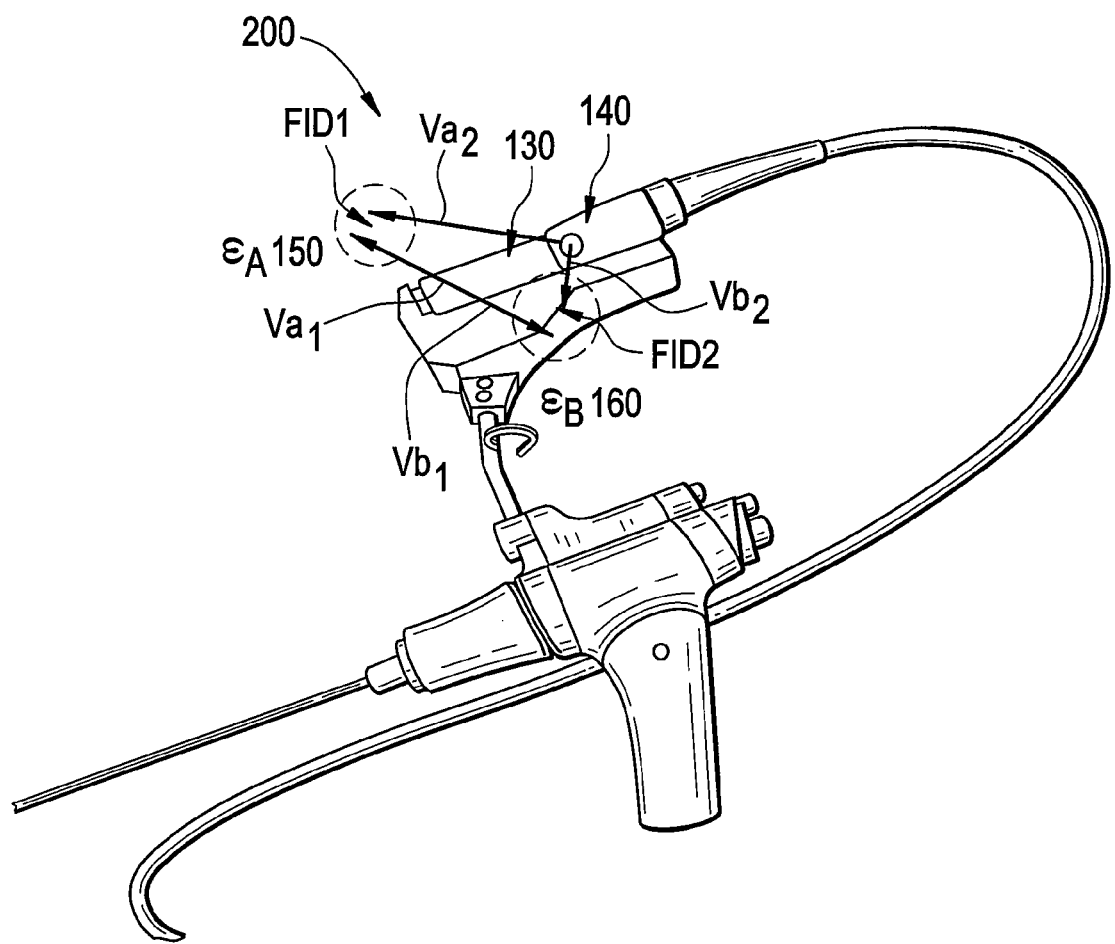
FIG. 2 illustrates a medical instrument with a vector model corresponding to FIG. 1

FIG. 2 illustrates a medical instrument 200 with a vector model corresponding to FIG. 1. The medical instrument of FIG. 2 is a Debrider used in sinus surgery procedure. Sensors 130 and 140 are shown attached to the medical instrument 200. Associated vectors $V_{a1}$, $V_{b1}$, $V_{a2}$, and $V_{b2}$ are shown projecting to virtual points 150 and 160, respectively. Graphically, FID1 and FID2 values are also shown. As illustrated above, if the FID is greater than a predetermined value ($\epsilon_A$ or $\epsilon_B$ in this example), the presence of an error condition may be indicated to a user. For example, if FID 1 is greater than a threshold distance $\epsilon_A$ the user may be alerted that an error condition is present and the navigation system is not currently accurate. Graphically, the circle 150 represents the threshold distance $\epsilon_A$. In an embodiment, system operation may be suspended. In addition, for example, if FID 2 is greater than a threshold distance $\epsilon_B$ the user may be alerted that an error condition is present and the navigation system is not currently accurate. Graphically, the circle 160 represents the threshold distance $\epsilon_B$ Similar to the FID 1 condition, in an embodiment, system operation may be suspended.

As is illustrated in FIGS. 1 and 2, generally only two virtual points, and thus two FID measurements, are used to detect error conditions. In addition, the virtual points are predefined and fixed, and may not be adjusted for more accurate readings based on various instrument attachments. The limitations of the system 100 as illustrated in FIGS. 1 and 2 may lead to false detection of error conditions, unnecessarily disrupting a physician during surgery and depriving a physician of the electromagnetic tracking system while conducting image-guided surgery.

Due to the nature of the non-linear EM distortion problems and adverse EM environment in the operating room, it is often challenging for a single distortion detection architecture to accurately and reliably sense the possible EM distortion field patterns. To improve the sensitivity of distortion detection, one may increase the number of FID measurements by generating more virtual points in the navigation space. One may also increase the number of monitoring sensors around the tracking sensors. As a result, the number of FIDs may be increased. As the number of FIDs increase, the sensitivity of the EM distortion detection may also increase.

Figure 3:
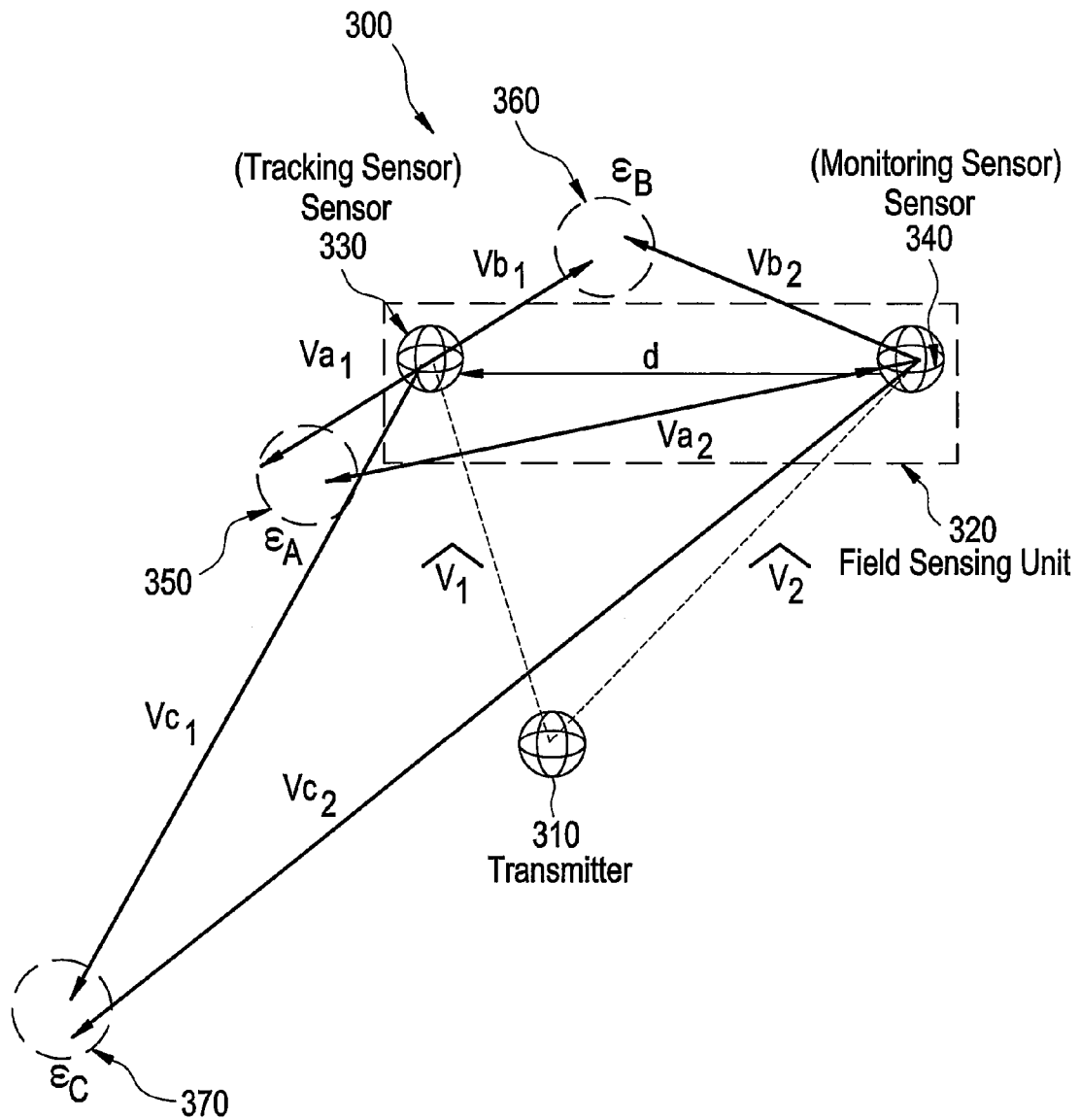
FIG. 3 illustrates a vector model in accordance with an embodiment of the present invention

FIG. 3 illustrates a vector model of an electromagnetic tracking system 300 in accordance with an embodiment of the present invention. The tracking system 300 has architecture of two sensors 330 and 340, and three virtual points 350, 360, and 370. The tracking system 300 includes a transmitter 310 and a field-sensing unit 320. In an embodiment, the transmitter 310 may be attached to patient anatomy. Additionally, in an embodiment, the field-sensing unit 320 may be attached to a medical instrument. As illustrated in FIG. 3, the field-sensing unit 320 may include two sensors, a tracking sensor 330 and a monitoring sensor 340. The sensors 330 and 340 may be separated by a fixed distance d. Although a two sensor, three virtual point architecture is illustrated in FIG. 3, the architecture includes any embodiment where a plurality of sensors is used to create a plurality of virtual points, where at least one of the virtual points is a non-fixed virtual point. Accordingly, it is contemplated that a two-sensor architecture may have one fixed virtual point and one non-fixed virtual point. It is also contemplated that any number of sensors may project any number of virtual points, so long as at least one of the virtual points is a non-fixed virtual point. The components of the embodiment 300 may be implemented alone or in combination, in hardware, firmware, and/or as a set of instructions in software, for example.

As illustrated by the vector model 300 in FIG. 3, the tracking sensor 330 and the monitoring sensor 340 may each project virtual vectors. The virtual vectors generally begin at a sensor and terminate at a virtual point. The termination point of a virtual vector may be a virtual tip ($V_{tip}$). A virtual tip may have a range of values and still be within a virtual point.

For example, the tracking sensor 330 may project vectors $V_{a1}$, $V_{b1}$ and $V_{c1}$. The monitoring sensor 340 may project vectors $V_{a2}$, $V_{b2}$ and $V_{c2}$. Three virtual points are illustrated in FIGS. 3, 350, 360, and 370. The scope of each of the virtual points is represented by circles 350, 360, and 370, respectively. As shown in FIG. 3, the $V_b$ vectors project to virtual point 360. The $V_a$ vectors project to virtual point 350. The $V_C$ vectors project to virtual point 370. The distance between the tips of the $V_a$ vectors is distance $\epsilon_A$. The distance between the tips of the $V_b$ vectors is distance $\epsilon_B$. The distance between the tips of the $V_c$ vectors is distance $\epsilon_c$.

The value of vectors $V_{a1}$, $V_{b1}$, $V_{c1}$, and $V_{a2}$, $V_{b2}$, $V_{c2}$ may be monitored as a medical instrument navigates through the transmitter coordinate system. In an embodiment, the vectors $V_{a1}$, $V_{b1}$, $V_{c1}$, and $V_{a2}$, $V_{b2}$, $V_{c2}$ may be monitored according to the following equations:

$$\hat{V}a_{(1)} = \hat{V}_1 + \hat{q}_1 \cdot V\text{tip}_{a1} \cdot \hat{q}_1^*$$

$$\hat{V}b_{(1)} = \hat{V}_1 + \hat{q}_1 \cdot V\text{tip}_{b1} \cdot \hat{q}_1^*$$

$$\hat{V}c_{(1)} = \hat{V}_1 + \hat{q}_1 \cdot V\text{tip}_{c1} \cdot \hat{q}_1^* \quad \text{Equation (4)}$$

$$\hat{V}a_{(2)} = \hat{V}_2 + \hat{q}_2 \cdot V\text{tip}_{a2} \cdot \hat{q}_2^*$$

$$\hat{V}b_{(2)} = \hat{V}_2 + \hat{q}_2 \cdot V\text{tip}_{b2} \cdot \hat{q}_2^*$$

$$\hat{V}c_{(2)} = \hat{V}_2 + \hat{q}_2 \cdot V\text{tip}_{c2} \cdot \hat{q}_2^* \quad \text{Equation (5)}$$

where $V_1$, $V_2$ and $q_1$, $q_2$ are Position and Orientation readings from sensor 330 and sensor 340, respectively. The $V_{tip}$ values represent the location of the tip of each of the respective vectors. For example, in the embodiment in which 370 is located at the instrument tip, vectors $V_{tipc1}$ and $V_{tipc2}$ are the instrument tip-offsets pointed from the tracking sensor 330 and monitoring sensor 340 to the tip of the instrument, respectively.

In an embodiment, the virtual point 370 is a non-fixed virtual point. A non-fixed virtual point is a virtual point that allows the parameters that define the virtual point to be adjusted. For example, a non-fixed virtual point may allow its location to be adjusted by adjusting the length and direction of the virtual vectors defining the virtual point. A non-fixed virtual point may be contrasted with a fixed virtual point. A fixed virtual point does not allow its parameters to be adjusted. In an example, the location of a fixed virtual point is fixed and the length and direction of the virtual vectors defining the virtual point may not be adjusted.

In an embodiment, a non-fixed virtual point may be located at strategic locations on the tracking instrument. For example, a non-fixed virtual point may be located at the tip of a surgical instrument. If during surgery, the surgeon alters the location of the tip of the surgical instrument, by utilizing an attachment, the virtual point may be adjusted to correspond with the location of the tip of the attachment. As shown in FIG. 3, the virtual point 370 may be adjusted according to the location of the tip of the surgical instrument. The location of the virtual point 370 may be adjusted for various instrument attachments that may alter the location of the instrument tip.

In an embodiment, the location of a non-fixed virtual point may be determined based on the medical instrument in use. For example, a user may communicate to computer software the type of medical instrument being used. Based on that information, the computer software may determine the location of the non-fixed virtual points. In addition, a user may communicate to computer software the type of instrument being used, and the type of attachment being used for that instrument. In such a case, the computer software may alter the location of the non-fixed virtual point based on the attachment in use for the medical instrument in use. In such a manner, a user may input the instrument type, and attachment profile, and the computer software may generate the locations of the non-fixed virtual points. Alternatively, a user may use a calibration tool to indicate to the computer software the desired locations of the virtual points. The computer software may then generate vector parameters for locating a virtual point at the desired location.

In the embodiment shown in FIG. 3, the location of the non-fixed virtual point 370 may be determined based on the type of instrument being used. Also, the location of the non-fixed virtual point 370 may be determined according to the type of attachment being used. The computer software may reside in a processor as part of the system 300. The processor may perform processing operations.

In the embodiment illustrated in FIG. 3, by adding the additional virtual point 370 at the instrument tip, the tracking system 300 may become more sensitive to a disturbance and more accurate to sense the magnitude of instrument tip error. It is contemplated that more than one non-fixed virtual point may be used. It is also contemplated that a non-fixed virtual point may be located at locations other than the instrument tip.

As shown in FIG. 1, by monitoring the difference between the vectors at the virtual points, the distortion of the transmitter coordinate system may be determined. In FIG. 3, the distance between the tips of the $V_a$ vectors is distance $\epsilon_A$. The distance between the tips of the $V_b$ vectors is distance $\epsilon_B$. The distance between the tips of the $V_c$ vectors is distance $\epsilon_C$. A test on the integrity of the transmitter field in FIG. 3 may be determined by the following equation:

$$\text{Test} = \begin{cases} FID\ 1 = |\hat{V}a_{(2)} - \hat{V}a_{(1)}| > \varepsilon A \\ \text{or} \\ FID\ 2 = |\hat{V}b_{(2)} - \hat{V}b_{(1)}| > \varepsilon B \\ \text{or} \\ FID\ 3 = |\hat{V}c_{(2)} - \hat{V}c_{(1)}| > \varepsilon C \end{cases} \quad \text{Equation (6)}$$

A quantifiable level of FID values may be used to determine the presence of potential error sources, such as metal distortion caused by the presence of a medical instrument. In an embodiment, a processor may perform the FID calculations. For example, if the FID is greater than a predetermined value ($\epsilon$), the presence of an error condition may be indicated to a user. For example, if FID 1 is greater than a distance $\epsilon_A$ the system 300 may alert the user that an error condition is present and the navigation system is not currently accurate. In addition, for example, if FID 2 is greater than a distance $\epsilon_B$ the system 300 may alert the user that an error condition is present and the navigation system is not currently accurate. If FID 3 is greater than a distance $\epsilon_C$ the system 300 may alert the user that an error condition is present and the navigation system is not currently accurate.

As sensors 330 and 340 are separated by a fixed distance d, the value of vectors $V_{a1}$, $V_{b1}$, and $V_{a2}$, $V_{b2}$, to remain at virtual points 350 and 360 may be determined as part of a factory calibration in a distortion free environment. However, in an embodiment, as virtual point 370 is adjustable, the value of vectors $V_{c1}$ and $V_{c2}$ to remain at virtual point 370 may be determined as part of an on-site calibration in a distortion free environment. The distortion-free environment may be controlled by the user following a calibration protocol. The FID 1 and FID 2 described in the previous sections may be used to monitor the integrity of calibration setup. The on-site calibration allows the virtual point 370 and vectors $V_{c1}$ and $V_{c2}$ to be adjusted based on the length and direction of the instrument tip-offset vectors pointed from the field sensing unit 320 to the instrument tip. In an embodiment, the location of the virtual point 370 may be predetermined according to instrument and attachment. A user may input the type of instrument being used and the type of attachment being used, and the system 300 may generate the location of the virtual point 370. In another embodiment, the user may indicate to the system 300 the desired location of the virtual point 370. A user may use a calibration tool to signal to the system 300 the desired location of the virtual point 370.

Figure 4:
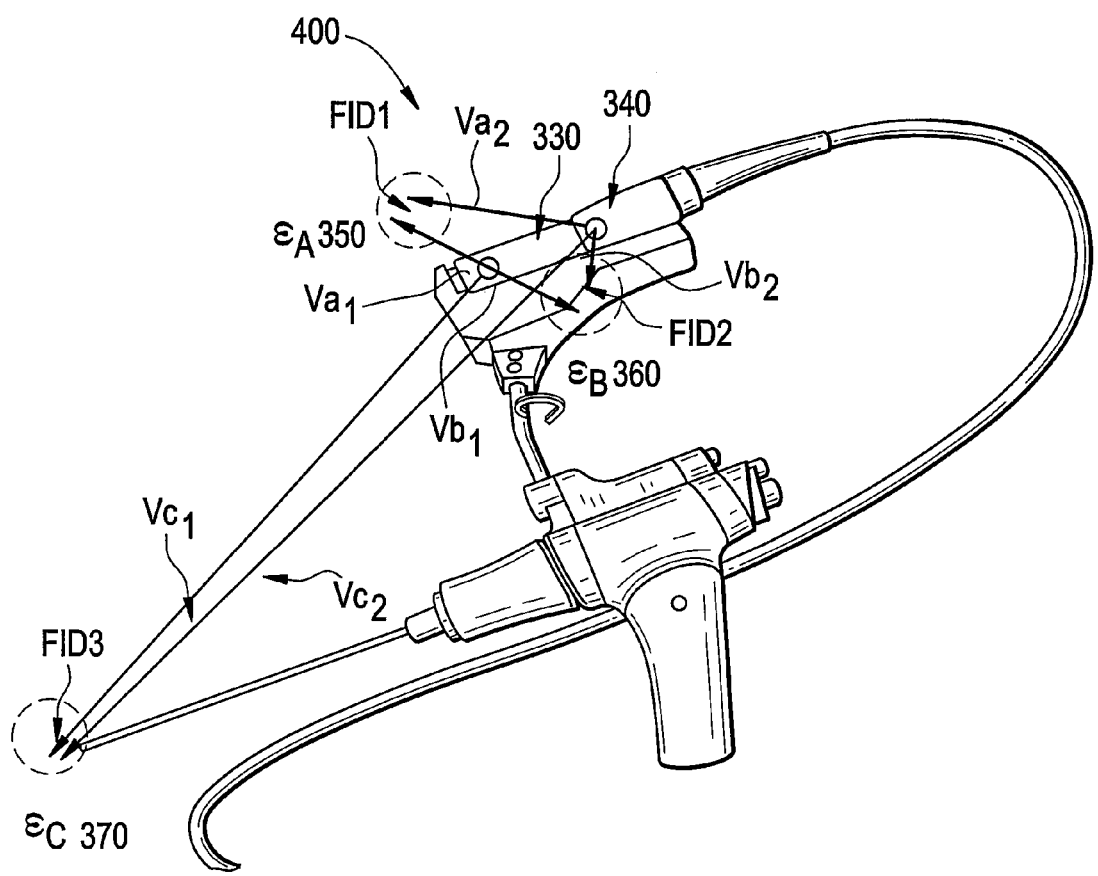
FIG. 4 illustrates a medical instrument with a vector model corresponding to FIG. 3

FIG. 4 illustrates a medical instrument 400 with a vector model corresponding to FIG. 3. The medical instrument of FIG. 4 is a Debrider used in sinus surgery procedure. The embodiment as shown in FIG. 4 may be implemented alone or in combination in hardware, firmware, and/or as a set of instructions in software, for example. Although the Debrider is shown in FIG. 4, any medical instrument may be used in conjunction with embodiments of the present invention.

Sensors 330 and 340 are shown attached to the medical instrument 400. Sensors 330 and 340 are illustrated at a fixed distance from each other. Associated vectors $V_{a1}$, $V_{b1}$, $V_{a2}$, and $V_{b2}$ are shown pointing to virtual points 350, 360, and 370. Graphically, FID1, FID2, and FID3 values are also shown. As illustrated above, if the FID is greater than a predetermined value ($\epsilon_A$, $\epsilon_B$, or $\epsilon_C$ in this example), the presence of an error condition may be indicated to a user. For example, if FID 1 is greater than a threshold distance $\epsilon_A$ the user may be alerted that an error condition is present and the navigation system is not currently accurate. Graphically, the circle 350 represents the threshold distance $\epsilon_A$. In an embodiment, system operation may be suspended. In addition, for example, if FID 2 is greater than a threshold distance $\epsilon_B$ the user may be alerted that an error condition is present and the navigation system is not currently accurate. Graphically, the circle 360 represents the threshold distance $\epsilon_B$. Similar to the FID 1 condition, in an embodiment, system operation may be suspended. Moreover, for example, if FID 3 is greater than a threshold distance $\epsilon_C$ the user may be alerted that an error condition is present and the navigation system is not currently accurate. Graphically, the circle 370 represents the threshold distance $\epsilon_C$. Similar to the FID 1 condition, in an embodiment, system operation may be suspended.

As is demonstrated, the non-fixed virtual point 370 is adjustable and may be located at the tip of the Debrider blade depending the surgical procedure and the attachment being used. For example, in the embodiment shown in FIG. 4, a straight blade is demonstrated. The non-fixed virtual point 370 is shown at the tip of the straight blade. Other blades may be used, however, with the Debrider. For example, a curved blade, a long blade, or a short blade may be used by surgeons. In an embodiment, each of the different blades may have different lengths. As such, each of the different blades may have different non-fixed virtual point locations. A non-fixed virtual point may be located at the tip of a medical instrument wherein the tip is for insertion into a patient anatomy. In such a manner, a user may obtain knowledge of errors at critical locations in the tracking system.

In an embodiment, a user may adjust the virtual point 370 by interacting with a computer through a user interface. In an example, a user may enter the instrument being used into a computer. The user may enter the attachment, or lack thereof, that is being used with the instrument. In an embodiment, the software in the computer may associate the instrument tip with a predetermined non-fixed virtual point. The non-fixed virtual point 370 may then be adjusted to the desired location. For example, a user may input that the instrument type is a Debrider blade. A user may indicate that the blade type is a straight blade. The computer software may generate a non-fixed virtual point location 370 equal to the instrument tip with the straight blade. If the user desires to change from a straight blade to a long blade, a user may input the change into the computer software, and the software may adjust the non-fixed virtual point location 370 to encompass the tip of the long blade. In such a manner, a user may monitor the error conditions at the tip of the instrument. A user may interact with a computer through computer keyboard, mouse, voice recognition, or other human-computer user interface.

In another embodiment, the user may indicate to the system 300 the desired location of the virtual point 370. A user may use a calibration tool to signal to the system 300 the desired location of the non-fixed virtual point 370. For example, the user may utilize a calibration pointer and touch the location of the medical instrument with the calibration pointer. The calibration pointer may then return the location of the desired virtual point 370 to the processor. The processor may generate the parameters to locate the non-fixed virtual point at the desired location.

Figure 5:
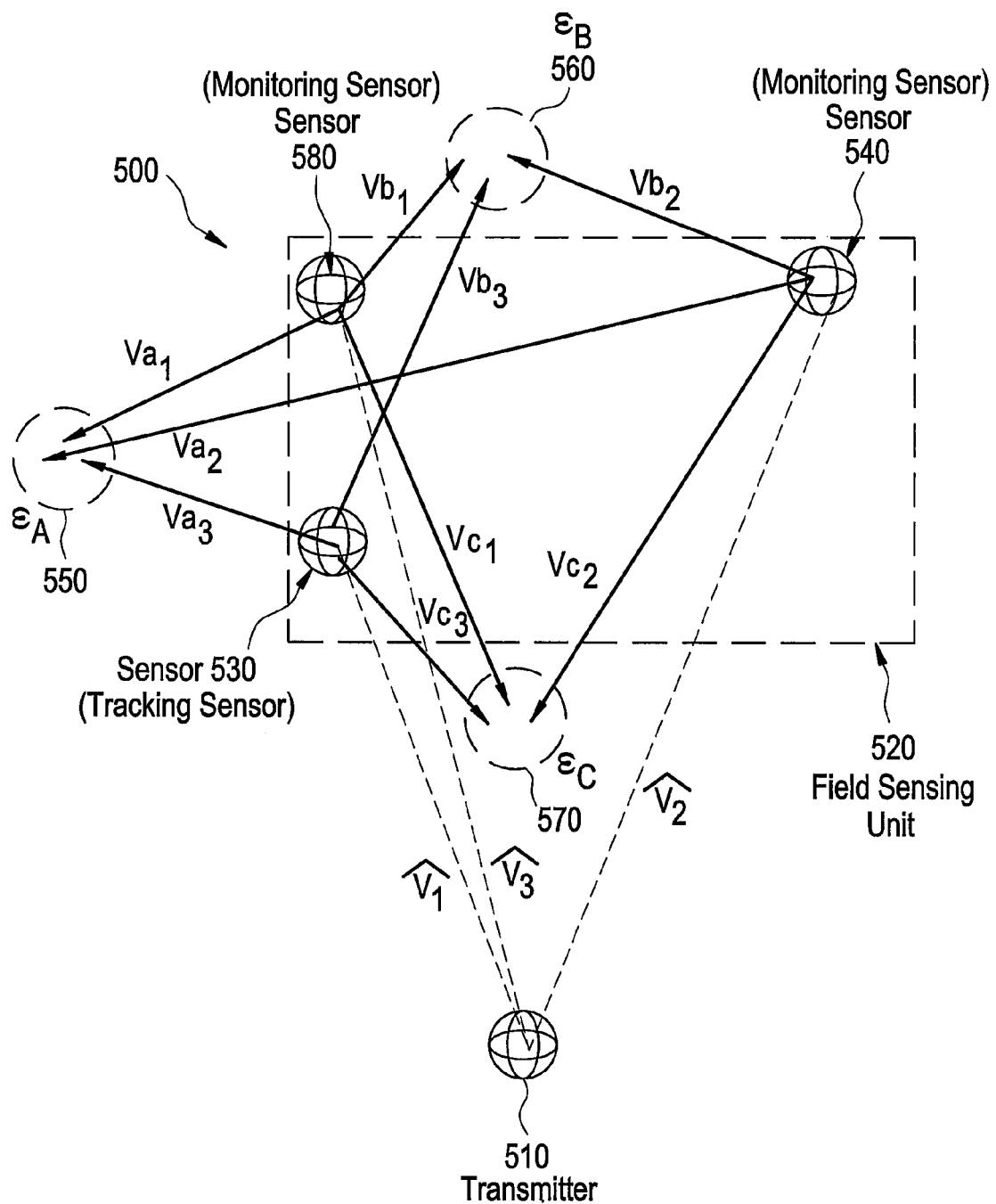
FIG. 5 illustrates a vector model in accordance with an embodiment of the present invention

FIG. 5 illustrates a vector model of an electromagnetic tracking system 500 in accordance with an embodiment of the present invention. The tracking system 500 has architecture of three sensors 530, 540, and 580 and three virtual points 550, 560, and 570. The tracking system 500 includes a transmitter 510 and a field-sensing unit 520. In an embodiment, the transmitter 510 may be attached to patient anatomy. Additionally, in an embodiment, the field-sensing unit 520 may be attached to a medical instrument. As illustrated in FIG. 5, the field-sensing unit 520 may include three sensors, a tracking sensor 530, a first monitoring sensor 540, and a second monitoring sensor 580.

Although a three sensor, three virtual point architecture is illustrated in FIG. 5, the architecture includes any embodiment the field sensing unit 520 has more than two sensors. It is contemplated that a field-sensing unit having more than two sensors may create a plurality of virtual points. It is also contemplated that at least one of the virtual points is a non-fixed virtual point. The components of the embodiment 500 may be implemented alone or in combination, in hardware, firmware, and/or as a set of instructions in software, for example.

In an embodiment, the tracking sensor 530 may project vectors $V_{a3}$, $V_{b3}$ and $V_{c3}$. The first monitoring sensor 540 may project vectors $V_{a2}$, $V_{b2}$ and $V_{c2}$. The second monitoring sensor 580 may project vectors $V_{a1}$, $V_{b1}$ and $V_{c1}$. Three virtual points are illustrated in FIGS. 5, 550, 560, and 570. The scope of each of the virtual points is represented by circles 550, 560, and 570, respectively. As shown in FIG. 5, the $V_b$ vectors project to virtual point $\epsilon_B$. The $V_a$ vectors project to virtual point $\epsilon_A$. The $V_C$ vectors project to virtual point $\epsilon_C$. The distance between the tips of the $V_a$ vectors is distance $\epsilon_A$. The distance between the tips of the $V_b$ vectors is distance $\epsilon_B$. The distance between the tips of the $V_c$ vectors is distance $\epsilon_C$.

The value of vectors $V_{a1}$, $V_{b1}$, $V_{c1}$ and $V_{a2}$, $V_{b2}$, $V_{c2}$ may be monitored as a medical instrument navigates through the transmitter coordinate system. In an embodiment, the vectors $V_{a1}$, $V_{b1}$, $V_{c1}$, and $V_{a2}$, $Vb_2$, $V_{c2}$ may be monitored according to the following equations:

$$\hat{V}a_{(1)} = \hat{V}_1 + \hat{q}_1 \cdot V\text{tip}_{a1} \cdot \hat{q}_1^*$$

$$\hat{V}b_{(1)} = \hat{V}_1 + \hat{q}_1 \cdot V\text{tip}_{b1} \cdot \hat{q}_1^*$$

$$\hat{V}c_{(1)} = \hat{V}_1 + \hat{q}_1 \cdot V\text{tip}_{c1} \cdot \hat{q}_1^* \quad \text{Equation (7)}$$

$$\hat{V}a_{(2)} = \hat{V}_1 + \hat{q}_2 \cdot V\text{tip}_{a2} \cdot \hat{q}_2^*$$

$$\hat{V}b_{(2)} = \hat{V}_2 + \hat{q}_2 \cdot V\text{tip}_{b2} \cdot \hat{q}_2^*$$

$$\hat{V}c_{(2)} = \hat{V}_2 + \hat{q}_2 \cdot V\text{tip}_{c2} \cdot \hat{q}_2^* \quad \text{Equation (8)}$$

$$\hat{V}a_{(1)} = \hat{V}_1 + \hat{q}_1 \cdot V\text{tip}_{a1} \cdot \hat{q}_1^*$$

$$\hat{V}a_{(1)} = \hat{V}_1 + \hat{q}_1 \cdot V\text{tip}_{a1} \cdot \hat{q}_1^*$$

$$\hat{V}a_{(1)} = \hat{V}_1 + \hat{q}_1 \cdot V\text{tip}_{a1} \cdot \hat{q}_1^* \quad \text{Equation (9)}$$

where $V_1$, $V_2$, $V_3$ and $q_1$, $q_2$, $q_3$ are Position and Orientation readings from sensor 540, sensor 550, and sensor 580, respectively. The $V_{tip}$ values represent the location of the tip of each of the respective vectors.

As shown above, by monitoring the difference between the vectors at the virtual points, the distortion of the transmitter coordinate system may be determined. For example, a test on the integrity of the transmitter field in FIG. 5 may be determined by the following equation:

$$Test = \begin{cases} FID\ 1 = |\hat{V}a_{(2)} - \hat{V}a_{(1)}| > \varepsilon A \\ FID\ 2 = |\hat{V}a_{(3)} - \hat{V}a_{(2)}| > \varepsilon A \\ FID\ 3 = |\hat{V}a_{(1)} - \hat{V}a_{(3)}| > \varepsilon A \\ FID\ 4 = |\hat{V}b_{(2)} - \hat{V}b_{(1)}| > \varepsilon B \\ \ldots \\ FID\ 9 = |\hat{V}c_{(1)} - \hat{V}c_{(3)}| > \varepsilon C \end{cases} \quad \text{Equation (10)}$$

A quantifiable level of FID may be used to determine the presence of potential error sources, such as metal distortion caused by the presence of a medical instrument. In an embodiment, a processor may perform the FID calculations. For example, if the FID is greater than a predetermined value ($\epsilon$), the presence of an error condition may be indicated to a user. For example, if FID 1 is greater than a distance $\epsilon_A$ the system 500 may alert the user that an error condition is present and the navigation system is not currently accurate. In addition, for example, if FID 2 is greater than a distance $\epsilon_B$ the system 500 may alert the user that an error condition is present and the navigation system is not currently accurate. If FID 3 is greater than a distance $\epsilon_C$ the system 500 may alert the user that an error condition is present and the navigation system is not currently accurate.

In the embodiment shown in the system 500, any of the sensors 530, 540, or 580 may have fixed or non-fixed virtual points. In an embodiment, all sensors 530, 540, and 580 have fixed virtual points. Alternatively, all sensors 530, 540, and 580 have non-fixed virtual points. In yet another embodiment, some combination of fixed and non-fixed virtual points may be projected from sensors 530, 540, and 580. The various configurations of virtual points, the locations of the virtual points, and whether the virtual points are fixed or non-fixed may be determined based on the medical instrument in use and whether an attachment for the medical instrument is being used.

Figure 6:
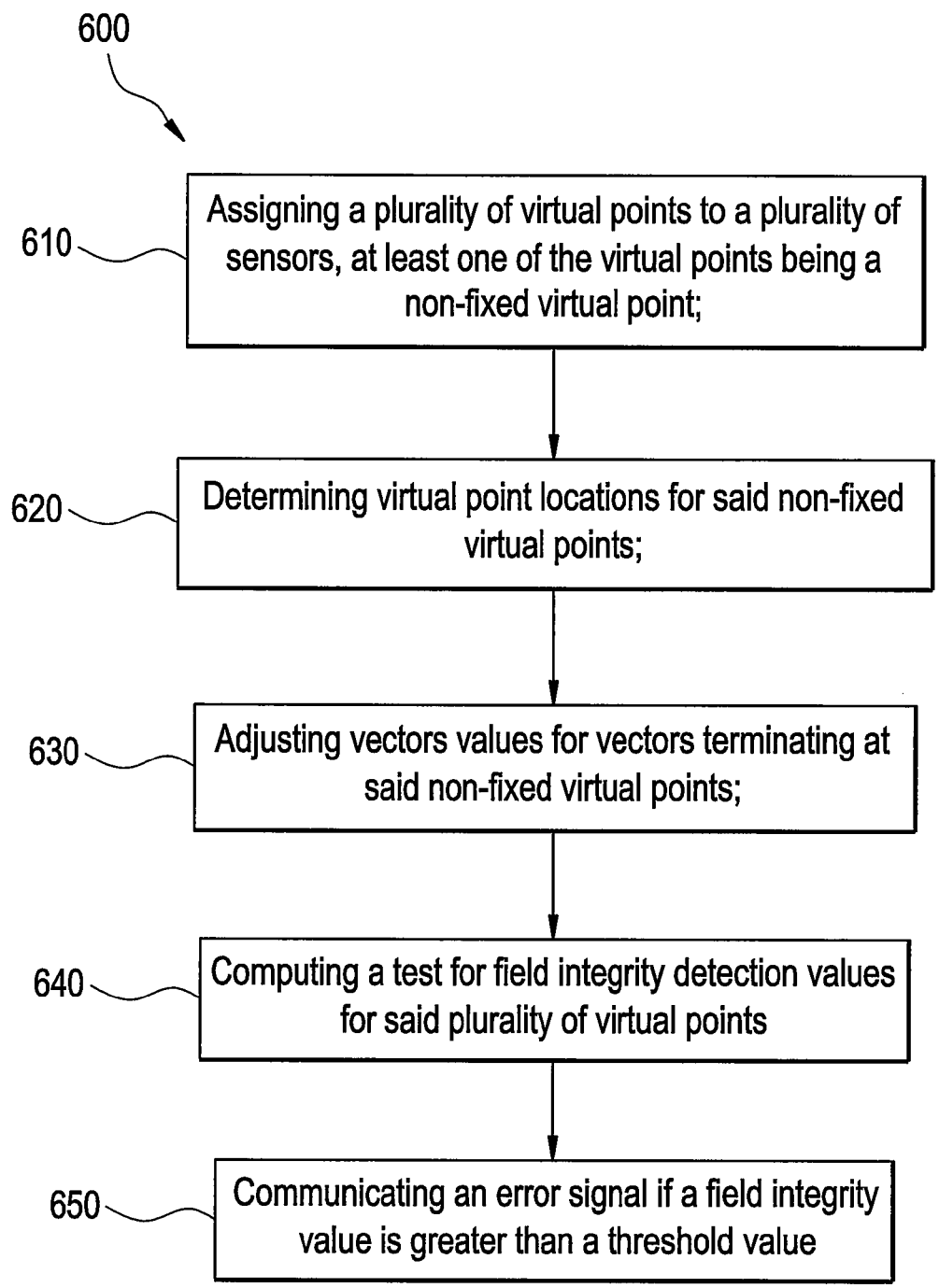
FIG. 6 illustrates a method in accordance with an embodiment of the present invention.

FIG. 6 illustrates a method 600 that may be used in accordance with an embodiment of the present invention. The method 600 may be implemented alone or in combination in hardware, firmware, and/or as a set of instructions in software, for example. At step 610, a plurality of virtual points is assigned to a plurality of sensors. At least one of the virtual points is a non-fixed virtual point. The step of assigning virtual points to a plurality of sensors includes determining the number of virtual points each sensor may project, and which virtual points are fixed and which virtual points are non-fixed.

A non-fixed virtual point is a virtual point that allows the parameters that define the virtual point to be adjusted. For example, a non-fixed virtual point may allow its location to be adjusted by adjusting the length and direction of the virtual vectors defining the virtual point. A non-fixed virtual point may be contrasted with a fixed virtual point. A fixed virtual point does not allow its parameters to be adjusted. In an example, the location of a fixed virtual point is fixed and the length and direction of the virtual vectors defining the virtual point may not be adjusted.

The assignment of virtual points to a plurality of sensors may include assigning virtual points based on the medical instrument being used. Additionally, the assignment of virtual points to a plurality of sensors may include assigning virtual points based on the attachment for a medical instrument being used.

At step 620, after the number of virtual points is assigned, the locations of the non-fixed virtual points may be determined. Fixed virtual points may have set locations that are generally not modifiable based on medical instrument type or user preference.

A non-fixed virtual point is a modifiable virtual point. The direction and length of the virtual point may be determined based on the type of medical instrument being used, or based oil user preference. In an embodiment, the location of a non-fixed virtual point may be determined based on the medical instrument being used. For example, a user may communicate to computer software the type of medical instrument being used. Based on that information, the computer software may determine the location of the non-fixed virtual points. In addition, a user may communicate to computer software the type of instrument being used, and the type of attachment being used for that instrument. In such a case, the computer software may alter the location of the non-fixed virtual point based on the attachment in use for the medical instrument in use. In such a manner, a user may input the instrument type, and attachment profile, and the computer software may generate the locations of the non-fixed virtual points. Alternatively, a user may use a calibration tool to indicate to the computer software the desired locations of the virtual points. The computer software may then generate vector parameters for locating a virtual point at the desired location.

At step 630, after the locations of the non-fixed virtual points are determined, the vector values for vectors terminating at non-fixed virtual points may be adjusted. The vector values may be adjusted so the vector tips terminate at the non-fixed virtual point locations. The vector values may include length of the vectors and the direction of the vectors.

At step 640, the field integrity detection values (FID values) are computed for the virtual points. As described above, by monitoring the difference between the vector tips at the fixed and non-fixed virtual points, the distortion of the transmitter coordinate system may be determined. Specifically, the difference between the vector tips is compared with a threshold value ($\epsilon$) to determine the level of distortion in the system. For example, a test on the integrity of the transmitter field may be determined by Equation 10.

At step 650, if a FID is greater than a threshold value, an error signal may be generated. For example, if the FID is greater than a set threshold, the presence of an error condition may be indicated to a user. In an embodiment, the threshold may be determined according to the type of medical instrument being used. Alternatively, a user may set the threshold.

The above embodiments are illustrative examples only and are not limiting on the scope of the present inventions. Any number of FIDs may be generated using any number of sensors and/or virtual points. It is also important to note that the system and method described above may be applied to optical or other types of position tracking systems used for medical or other applications.

In an alternative embodiment, the above described tracking systems and method may be used with virtual reality computer software. Virtual reality computer software includes a tracking coordinate system and a plurality of sensors that may project a plurality of virtual tips. In an embodiment, the instrument may consist of any object that may create distortion in a tracking coordinate system for use with virtual reality computer software.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A tracking system for instrument navigation, said system comprising:
   a transmitter for transmitting a signal, said signal identifying transmitter coordinates;
   a field sensing unit for determining the location of the field sensing unit within said transmitter coordinates, said field sensing unit having a plurality of sensors, said plurality of sensors creating a plurality of virtual points, at least one of said virtual points being a non-fixed virtual point; and
   a processor for processing field integrity detection values for said virtual points.

2. The system of claim 1, wherein said instrument is a medical instrument.

3. The system of claim 2, wherein said transmitter is configured to be attached to patient anatomy.

4. The system of claim 2, wherein said field sensing unit is attached to a medical instrument, and wherein said at least one of said virtual points is non-fixed with respect to said medical instrument.

5. The system of claim 2, wherein the location of the non-fixed virtual point is determined based on the medical instrument in use.

6. The system of claim 5, wherein the location of a non-fixed virtual point is based on the attachment in use for the medical instrument in use.

7. The system of claim 5, wherein the location of a non-fixed virtual point is at the tip of said medical instrument, said tip being used for insertion into a patient anatomy.

8. A tracking system for medical instrument navigation, said system comprising:
- a transmitter for transmitting a signal, said signal identifying transmitter coordinates;
- a field sensing unit secured to the medical instrument for determining the location of the field sensing unit within said transmitter coordinates, said field sensing unit having more than two sensors that create a plurality of virtual points, at least one of said virtual points being fixed with respect to the medical instrument, and at least another of said virtual points being non-fixed with respect to the medical instrument; and
- a processor for processing field integrity detection values for said virtual points.

9. The system of claim 8, wherein the location of the non-fixed virtual point is determined based on the medical instrument in use.

10. The system of claim 8, wherein the location of a non-fixed virtual point is at the tip of said medical instrument, said tip being used for insertion into a patient anatomy.

11. The system of claim 9, wherein the location of a non-fixed virtual point is based on the attachment in use for the medical instrument in use.

12. A method for instrument navigation, said method comprising using at least one processor to perform at least the following:
- assigning a plurality of virtual points to a plurality of sensors, at least one of the virtual points being a non-fixed virtual point;
- determining virtual point locations for said non-fixed virtual point;
- adjusting vector values for vectors terminating at said non-fixed virtual point;
- computing field integrity values for said plurality of virtual points; and,
- communicating an error signal if a field integrity value is greater than a threshold value.

13. The method of claim 12, wherein said instrument is a medical instrument.

14. The method of claim 12, wherein said instrument is a field sensing unit for use with virtual reality computer software.

15. The method of claim 13, wherein the step of assigning further includes indicating the medical instrument being used to computer software.

16. The method of claim 15, wherein the step of assigning includes indicating the attachment being used for the medical instrument to computer software.

17. The method of claim 15, wherein the step of determining virtual point locations includes determining virtual point locations based on the medical instrument being used.

18. The method of claim 16, wherein the step of determining virtual point locations includes determining virtual point locations based on the medical instrument attachment being used.

* * * * *